United States Patent
Gill

(10) Patent No.: US 9,463,100 B2
(45) Date of Patent: Oct. 11, 2016

(54) METHOD AND APPARATUS FOR CONTROLLING A PROSTHETIC DEVICE

(75) Inventor: Hugh Gill, Lothian (GB)

(73) Assignee: TOUCH BIONICS LIMITED, Livingston, West Lothian (GB)

( * ) Notice: Subject to any disclaimer, the term of this patent is extended or adjusted under 35 U.S.C. 154(b) by 152 days.

(21) Appl. No.: 14/236,138

(22) PCT Filed: Sep. 13, 2012

(86) PCT No.: PCT/GB2012/052263
§ 371 (c)(1),
(2), (4) Date: Apr. 29, 2014

(87) PCT Pub. No.: WO2013/038187
PCT Pub. Date: Mar. 21, 2013

(65) Prior Publication Data
US 2014/0288666 A1    Sep. 25, 2014

(30) Foreign Application Priority Data

Sep. 16, 2011 (GB) .................................. 1116069.4

(51) Int. Cl.
| | |
|---|---|
| A61F 2/68 | (2006.01) |
| A61F 2/72 | (2006.01) |
| A61F 2/58 | (2006.01) |
| A61F 4/00 | (2006.01) |
| A61F 2/70 | (2006.01) |

(52) U.S. Cl.
CPC .................. *A61F 2/72* (2013.01); *A61F 2/583* (2013.01); *A61F 2/68* (2013.01); *A61F 4/00* (2013.01); *A61F 2002/704* (2013.01)

(58) Field of Classification Search
CPC ............ A61F 2/68; A61F 2/72; A61F 2/583; A61F 2002/7695
See application file for complete search history.

(56) References Cited

U.S. PATENT DOCUMENTS

| | | |
|---|---|---|
| 2,669,727 A | 2/1954 | Opuszenski |
| 3,866,246 A | 2/1975 | Seamone et al. |
| 4,558,704 A | 12/1985 | Petrofsky |
| 4,623,354 A | 11/1986 | Childress et al. |
| 4,808,187 A | 2/1989 | Patterson et al. |

(Continued)

FOREIGN PATENT DOCUMENTS

| | | |
|---|---|---|
| CN | 1803413 | 7/2006 |
| EP | 0145504 | 6/1985 |

(Continued)

OTHER PUBLICATIONS

Connolly, "Prosthetic hands from Touch Bionics," Industrial Robot: An International Journal, 35(4):290-293, 2008.

(Continued)

*Primary Examiner* — Bruce E Snow
(74) *Attorney, Agent, or Firm* — K&L Gates LLP

(57) ABSTRACT

A prosthetic device control apparatus and method of controlling the same. The prosthetic device control apparatus (32) comprising an input interface (34) operable to receive input control signals and a detector (40) operable to determine if a prosthetic device (10) is operatively connected to the prosthetic device control apparatus, wherein the prosthetic device control apparatus is operable, responsive to the detector, to use the input control signals to control either a computer model (52) or movement of the operatively connected prosthetic device.

8 Claims, 7 Drawing Sheets

(56) References Cited

U.S. PATENT DOCUMENTS

| | | | |
|---|---|---|---|
| 4,955,918 | A | 9/1990 | Lee |
| 4,990,162 | A | 2/1991 | LeBlanc et al. |
| 5,413,611 | A * | 5/1995 | Haslam et al. ............ 623/25 |
| 5,888,246 | A | 3/1999 | Gow |
| 6,344,062 | B1 | 2/2002 | Abboudi et al. |
| 7,370,896 | B2 | 5/2008 | Anderson et al. |
| 7,922,773 | B1 | 4/2011 | Kuiken |
| 8,662,552 | B2 | 3/2014 | Torres-Jara |
| 2003/0036805 | A1 | 2/2003 | Senior |
| 2004/0078091 | A1 | 4/2004 | Elkins |
| 2005/0192677 | A1 | 9/2005 | Ragnarsdottir et al. |
| 2006/0158146 | A1 | 7/2006 | Tadano |
| 2006/0167564 | A1 | 7/2006 | Flaherty et al. |
| 2006/0212129 | A1 | 9/2006 | Lake et al. |
| 2008/0146981 | A1 | 6/2008 | Greenwald et al. |
| 2008/0262634 | A1 | 10/2008 | Puchhammer |
| 2010/0016990 | A1 | 1/2010 | Kurtz |
| 2010/0116078 | A1 | 5/2010 | Kim |
| 2010/0274365 | A1 | 10/2010 | Evans et al. |
| 2015/0142082 | A1 * | 5/2015 | Simon et al. ............ 607/61 |

FOREIGN PATENT DOCUMENTS

| | | |
|---|---|---|
| EP | 1043003 | 10/2000 |
| GB | 1585256 | 2/1981 |
| GB | 2444679 | 6/2008 |
| JP | 53-11456 | 2/1978 |
| WO | 95/24875 | 9/1995 |
| WO | 00/69375 | 11/2000 |
| WO | 03/017878 | 3/2003 |
| WO | 03/017880 | 3/2003 |
| WO | 2006/069264 | 6/2006 |
| WO | 2007/063266 | 6/2007 |
| WO | 2007/076764 | 7/2007 |
| WO | 2007/076765 | 7/2007 |
| WO | 2007/127973 | 11/2007 |
| WO | 2008/044207 | 4/2008 |
| WO | 2008/098059 | 8/2008 |
| WO | 2008/098072 | 8/2008 |
| WO | 2010/018358 | 2/2010 |
| WO | 2011/001136 | 1/2011 |
| WO | 2011/022569 | 2/2011 |
| WO | 2011/036473 | 3/2011 |
| WO | 2011/107778 | 9/2011 |

OTHER PUBLICATIONS

Stix, "Phantom Touch: Imbuing a Prosthesis with Manual Dexterity," Scientific American, Oct. 1998, pp. 41 and 44.
Search Report for GB Application No. GB0916895.6 dated Mar. 17, 2010, 5 pages.
Search Report for GB Application No. GB0910920.8 dated Mar. 26, 2010, 3 pages.
PCT International Search Report for PCT International Application No. PCT/GB2013/051961, mail date Dec. 11, 2013, 5 pages.
PCT International Search Report for PCT International Application No. PCT/GB2012/052021, mail date Nov. 26, 2012, 5 pages.
PCT Written Opinion of the International Searching Authority for PCT International Application No. PCT/GB2012/052021, mail date May 3, 2013, 6 pages.
PCT International Search Report for PCT International Application No. PCT/GB2012/052111, mail date Nov. 26, 2012, 5 pages.
PCT International Preliminary Report on Patentability for PCT International Application No. PCT/GB2010/051529, mail date Apr. 5, 2012, 7 pages.
PCT International Preliminary Report on Patentability for PCT International Application No. PCT/GB2011/050368, mail date Sep. 13, 2012, 7 pages.
PCT International Search Report and Written Opinion of International Searching Authority for PCT International Application No. PCT/GB2011/050368, mail date Jun. 21, 2011, 11 pages.
PCT International Search Report and Written Opinion of International Searching Authority for PCT International Application No. PCT/GB2010/001232, mail date Oct. 6, 2010, 9 pages.
PCT International Preliminary Report on Patentability for PCT International Application No. PCT/GB2010/001232, mail date Jan. 4, 2012, 6 pages.
PCT International Search Report and Written Opinion of International Searching Authority for PCT International Application No. PCT/GB2010/051529, mail date Jan. 4, 2011, 11 pages.

* cited by examiner

METHOD AND APPARATUS FOR CONTROLLING A PROSTHETIC DEVICE

CROSS REFERENCE TO RELATED APPLICATIONS

This application is a national phase under 35 U.S.C. 371 of International Application No. PCT/GB2012/052263 filed on Sep. 13, 2012, which claims priority to and benefit of GB Application No. 1116069.4 filed on Sep. 16, 2011, the entirety of these applications are incorporated by reference herein.

FIELD OF THE INVENTION

The present invention relates to methods of controlling a prosthetic device, prosthetic device control apparatus and systems, useable for example, in training of patients to control a prosthetic device.

BACKGROUND TO THE INVENTION

Prosthetic devices such as prosthetic hands, prosthetic partial hands and prosthetic fingers can have their movements controlled by electromyographic (EMG) signals. Such EMG signals may be measured by placing electrodes on the residual limb, or stump, of a human subject or patient. The EMG signals are then processed to control actuators that result in the of movement of a prosthetic device. Users of such myoelectric prosthetic devices typically need practice to control their muscles in order to generate the optimum EMG signals as measured by the electrodes. A patient can learn to control the intensity, pattern and timing of activation of one or more of their muscles in order to trigger the EMG signal. This practice may be time consuming, depending on the particular patient.

Prosthetic devices can be computer controlled so that they respond to complex patterns and timings of EMG signals. In order to use a limited set of control signal patterns to control a large number of possible movements (or movement features) of a prosthetic device, a profile may be used. A profile is an assignment of particular set of control signals, such as caused by a pattern of triggers (for example hold open, co-contract, double impulse and triple impulse) to respective movement features of the prosthetic device. For example, for a prosthetic hand the movement features are called grip features and may include, but are not limited to, pinch open, pinch closed, thumb open, thumb closed, "three way chuck" pinch open or closed, index point, natural hand and thumb parking. The profile, once set up by a patient, can thus be used to translate control signals triggered by muscle activity in the patient's residual limb into movements to particular selected positions (features) of the prosthetic device.

When a patient receives a new prosthetic device it takes them time to learn how to control the device. The procurement, fitting and manufacturing typically results in a long delay from the initial meeting with the prosthetist to the time when the patient can begin training to use the prosthetic by practicing its use. One problem with this is that a patient cannot use their prosthetic device with full control starting on the day that they eventually do receive it. Another problem is that when the training, which involves practicing using muscles in the residual limb, begins after the prosthetic device is delivered, the patient's muscles can change in shape as they develop in response to the training. This has the unfortunate effect of making the socket that mounts on the residual limb and onto which the prosthetic device is connected, cease to fit comfortably. This can result in another cycle of fitting, manufacture and delivery of a revised socket, thus delaying comfortable use of the prosthetic with full control. In the worst case, if the socket has to be taken away for remanufacture because it no longer fits, then the patient is unable to use the prosthetic device in the absence of the socket. Another problem is that the patient can get out of practice and may lose muscle tone when the prosthetic device is sent away for repair or servicing.

It would be advantageous to overcome at least some of the problems described above.

STATEMENT OF INVENTION

According to the first aspect of the present invention there is provided a method of controlling a prosthetic device, the method including:
  providing a computer model of a prosthetic device, the computer model operable to simulate movement of a prosthetic device responsive to control signals;
  providing a prosthetic device operable to move responsive to control signals;
  receiving input control signals;
  determining if the prosthetic device is operatively connected; and
  depending on the determination, using the input control signals to control either the computer model or movement of the prosthetic device.

The advantage of using the input control signals to control either the computer model or movement of the actual prosthetic device is that the patient can develop their muscle control and mental skills for controlling the prosthetic device whether or not the prosthetic device is operatively connected. This means that when a prosthetic device is not present, for example before its delivery or while it is away for repair, a patient may train or maintain their control skills and build muscle tone. Therefore, when the prosthetic device is first or again operatively connected, their control skills and muscles will be well prepared to immediately begin or resume using the prosthetic device with full control. This clearly has a benefit to the quality of life of the patient.

Preferably, if the prosthetic device is not operatively connected, controlling the computer model by providing output control signals arising from the input control signals to a processor operable to control the computer model.

The advantage of providing output control signals is that a processor, such as one remote from the patient, can receive the control signals so that it can control the computer model using them.

Preferably, if the prosthetic device is operatively connected, controlling the movement of the prosthetic device by providing power to the prosthetic device and providing output control signals arising from the input control signals to the prosthetic device.

The advantage of providing power to the prosthetic device is that the patient can control it as if it were attached to a socket that would normally provide power when in use. The advantage of providing output control signals is that the patient can control the prosthetic device in the same way as if it was attached via a socket to the patient's residual limb.

Preferably, if the prosthetic device is operatively connected, powering down circuitry operable to provide control signals arising from the input control signals to a processor operable to control the computer model.

The advantage of powering down the circuitry that is used to provide control signals for the computer model is to conserve power, that would otherwise be consumed by the circuitry, at the time it is not needed, when the prosthetic device is being controlled.

Preferably, the method further includes using a profile of control signal assignments to grip features to control the computer model and using the same profile to control the movement of the prosthetic device.

The advantage of using the same profile to control both the computer model and the movement of the prosthetic device is that the patient can develop their control skills and muscle tone in the absence of a prosthetic device, by using the computer model, so that they are well prepared when they begin or resume controlling and using the prosthetic device itself.

Preferably, the input control signals comprise electromyographic signals.

Electromyographic signals are convenient control signals for the control of prosthetic devices. However, the skilled person will appreciate that other signals arising from the brain and/or body of the patient and signals converted into electronic, optical or other form may be used as input control signals.

According to a second aspect of the present invention there is provided a prosthetic device control apparatus comprising:
an input interface operable to receive input control signals; and
a detector operable to determine if a prosthetic device is operatively connected to the prosthetic device control apparatus,
wherein the prosthetic device control apparatus is operable, responsive to the detector, to use the input control signals to control either a computer model or movement of the operatively connected prosthetic device.

Preferably, the prosthetic device control apparatus further comprises a communication interface operable, responsive to the detector, to provide output control signals arising from the input control signals to a processor operable to control the computer model.

Preferably, the prosthetic device control apparatus further comprises a prosthetic device interface operable, responsive to the detector, control the movement of the prosthetic device by providing output control signals arising from the input control signals to the prosthetic device.

Preferably, the prosthetic device interface is operable to provide power to the prosthetic device.

Preferably, the prosthetic device interface is arranged to connectably receive a prosthetic device.

Preferably, the prosthetic device control apparatus further comprises a processor operable to process the input control signals to generate the output control signals.

Preferably, the input control signals comprise electromyographic signals.

According to a third aspect of the present invention there is provided a prosthetic device control system comprising:
a prosthetic device control apparatus according to the second aspect; and
a computational arrangement comprising:
processor configured to receive control signals from the prosthetic device control apparatus;
a computer model operable to simulate movement of a prosthetic device; and
a computer program product comprising instructions which, when executed by the processor, causes the processor to control the computer model using the control signals.

Preferably, the computer program product further causes a display to display a representation of the computer model.

Preferably, the computer program product further causes the display to be refreshed at substantially the same rate as a rate of update of a prosthetic device.

Preferably, the computer program product further causes the processor to use profile of control signal assignments to grip features to control the computer model and to send the same profile to the prosthetic device.

BRIEF DESCRIPTION OF THE DRAWINGS

The present invention will now be described by way of example only with reference to the following drawings, of which.

SPECIFIC DESCRIPTION

Figure 1:
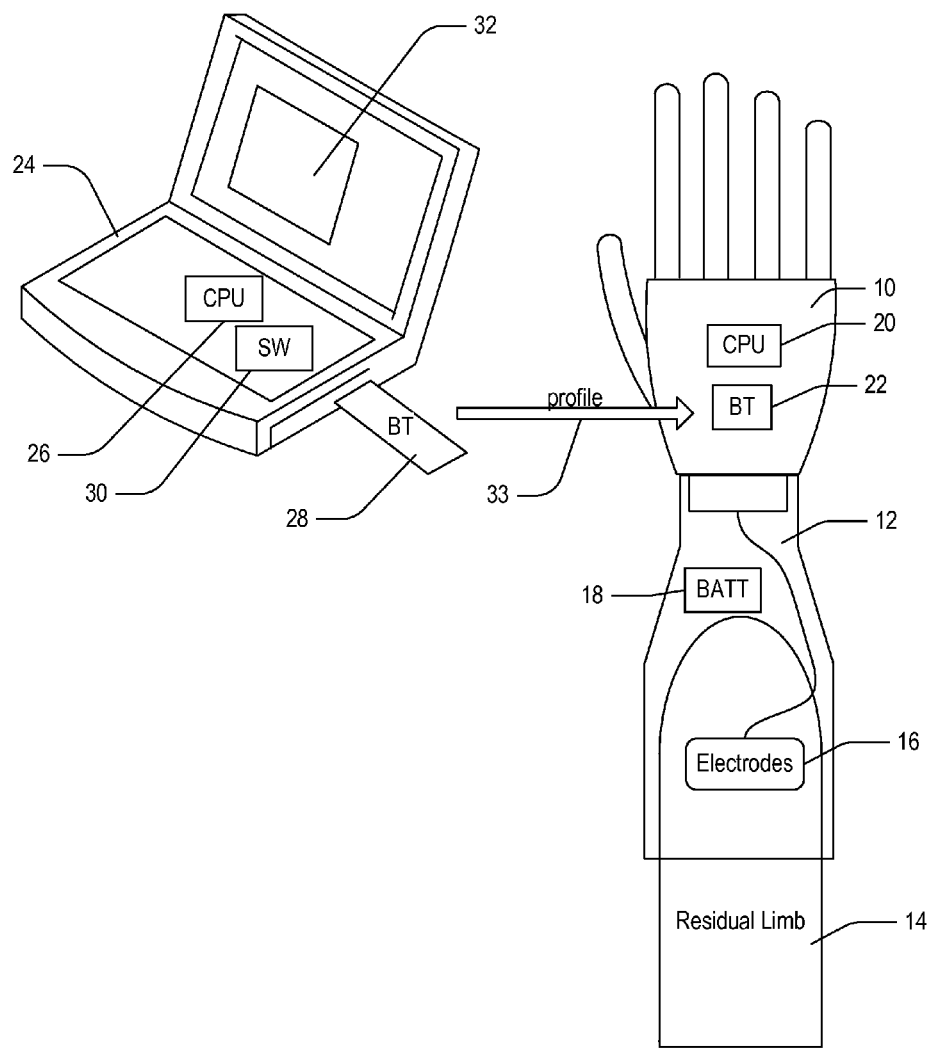
FIG. 1 illustrates a known programmable prosthetic including a prosthetic device and a socket.

With reference to FIG. 1, a prosthetic device 10, in this case a prosthetic hand, is operably connected to a socket 12 which fits on to the residual limb 14 of a patient. The prosthetic device and socket together may be referred to as a prosthetic. Electrodes 16 measure EMG signals that are conveyed to the prosthetic hand 10 along electrical wires. The socket 12 has a battery 18 that provides power to the prosthetic hand 10. The powered prosthetic hand 10 moves in response to the patient's muscle signals. The prosthetic hand has a processor 20 and a Bluetooth™ radio communication module 22. The processor uses the control signals from the electrodes to control the movement of the prosthetic hand by controlling motors (not shown), for example with one motor in each finger. A computer 24 has a processor 26 and a Bluetooth dongle 28. The computer runs software 30 with an interface 32 that allows the patient, prosthetist or occupational therapist to create a profile to assign control signals to grip features. The computer 24 under the control of the software 30 can send the profile 33 via a Bluetooth connection from dongle 28 to module 22. The processor 20 in the prosthetic hand can then update its firmware in accordance with the profile.

In the following Figures, where a feature is the same as in previous Figures, the same referencing numerals are used.

Figure 2:
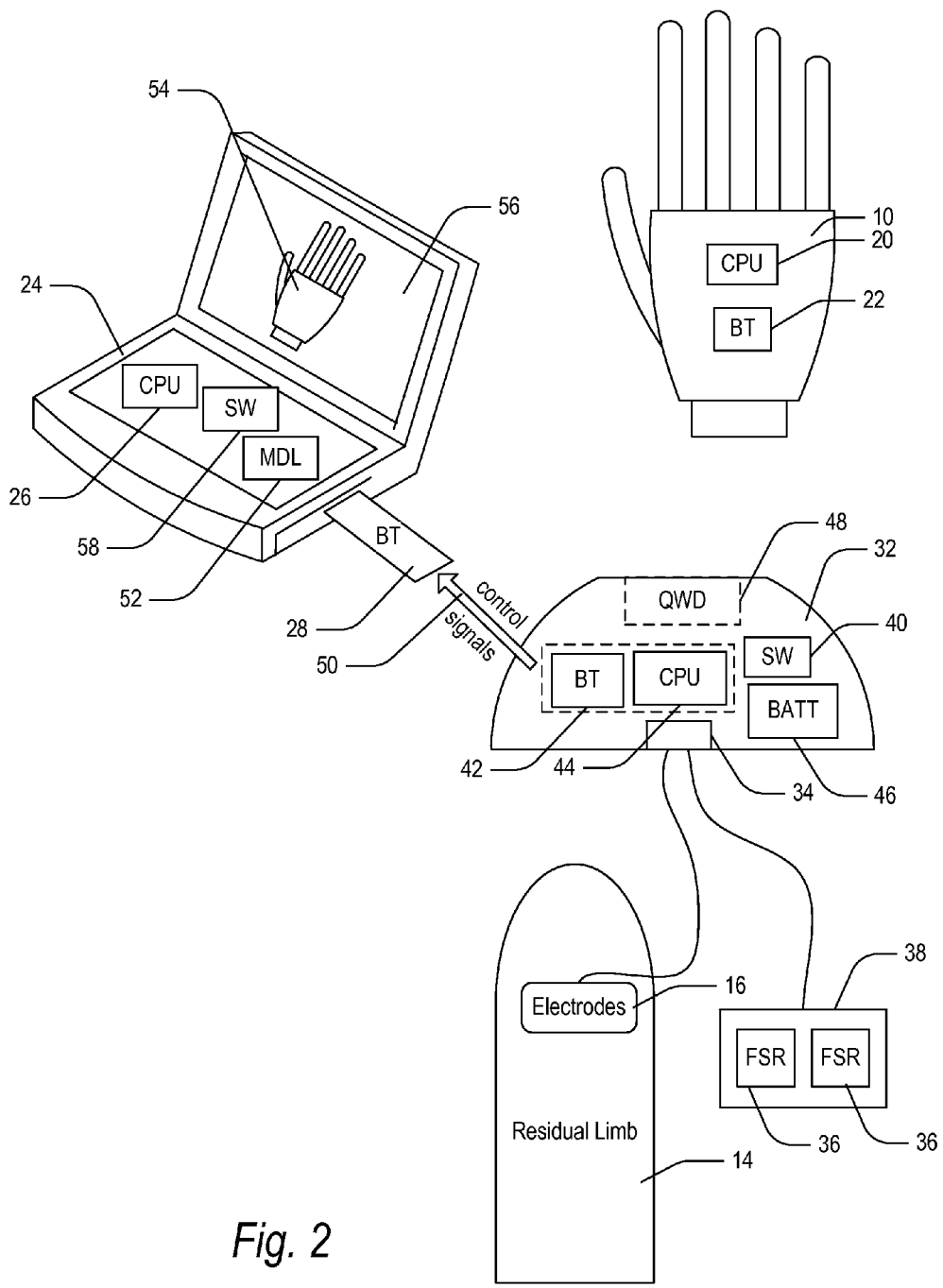
FIG. 2 illustrates a prosthetic device control system in accordance with an embodiment of the present invention.

With reference to FIG. 2, a prosthetic device control apparatus 32, in this example a dock, is provided with an input interface 34 that is operable to receive input control signals, in this example EMG signals, from electrodes 16 and simulated control signals from force sensitive resistors (FSRs) 36 on keypad 38. The prosthetic device 10 is shown disconnected from the dock 32. In an alternative arrangement (not shown), the prosthetic hand 10 may sit in the dock but be switched off with its on/off switch (not shown), so that although connected it is not operatively connected to the dock. The dock has a switch 40 that acts as a detector and determines if the prosthetic hand 10 is operatively connected to the dock 32. It will be apparent to one skilled in the art that the function of determining if a prosthetic device is operatively connected may be performed by another electrical or mechanical arrangement of sensors and/or switches, for example by sensing the presence of the prosthetic device and/or routing control signals.

The dock 32 also has a Bluetooth communication interface 42 and a processor 44. The dock also has a battery 46 and a prosthetic device interface 48, in this example referred to as a quick wrist disconnect (QWD) socket.

The switch 40 determines if a prosthetic device is operatively connected to the dock 32. When the prosthetic device 10 is not operatively connected to the dock, the switch detects this state and the dock provides output control signals 50 arising from the input control signals to the processor 26, which is operable to control a computer model 52. The processor 44 may be used processes the input signals to generate the output signals. The computer model 52 is operable to simulate movement of a prosthetic device. The computer 24 runs a program 58 to control the model and provides a real-time virtual three-dimensional animation 54 of a computer-aided design (CAD) generated prosthetic device model. The animation 54 is displayed on a display 56 of the computer 24. In this mode of operation, with the prosthetic hand 10 not operatively connected to the dock 32, the patient thus controls the animation 54 that is a representation of the computer model 52, via the electrodes 16 and the dock 32. The animation may have a frame rate substantially the same rate as the rate of update of the prosthetic device. This provides a realistic rendering of the prosthetic device and allows the user to develop their skills in the same way as if they were working with an actual prosthetic device.

Figure 3:
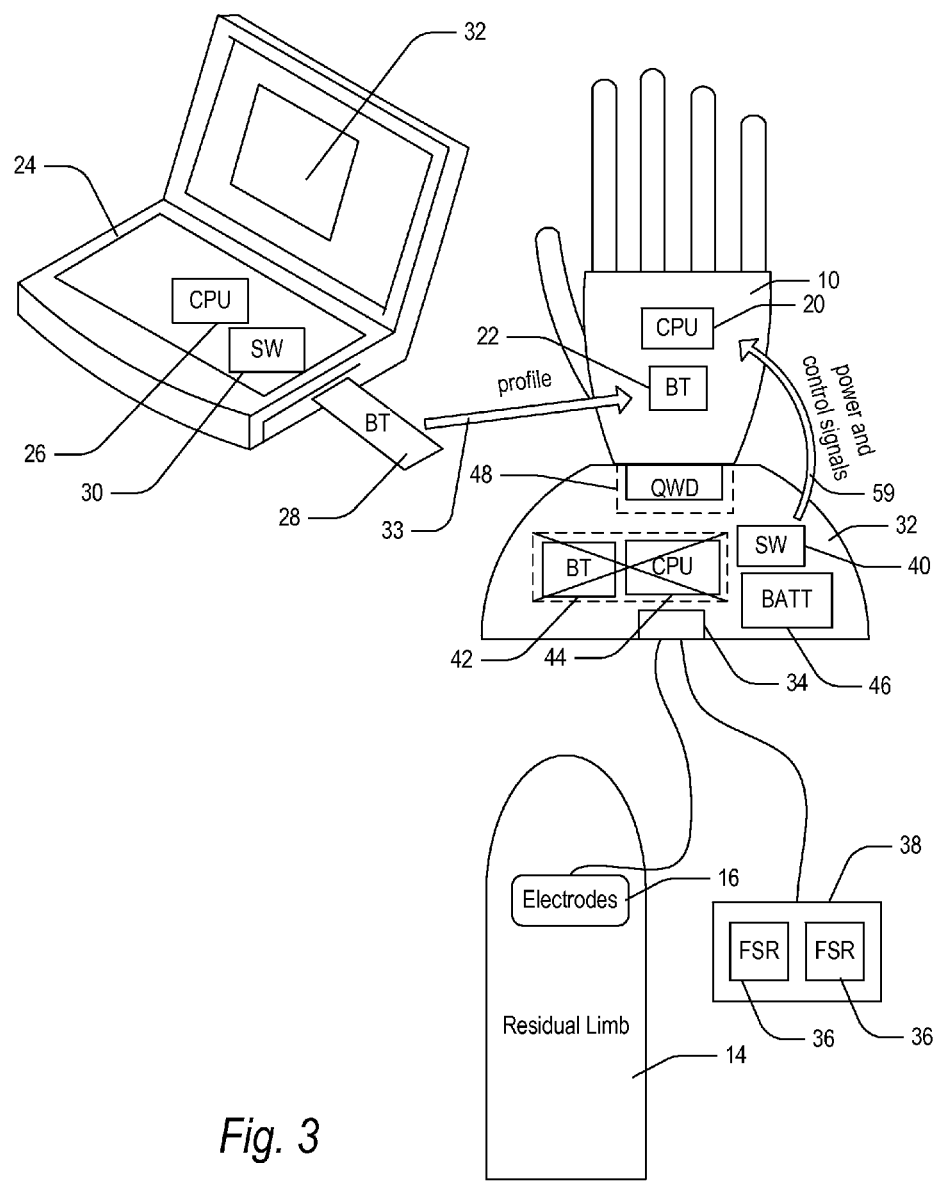
FIG. 3 illustrates the same prosthetic device control system as shown in FIG. 2, but with the prosthetic device operatively connected to the prosthetic device control apparatus.

With reference to FIG. 3, the prosthetic hand 10 is shown operatively connected to the dock 32 with the prosthetic hand 10 being inserted into the QWD socket 48, and in this example turned on with its on/off switch (not shown). The switch 40 determines that the prosthetic hand 10 is operatively connected. Optionally, the switch 40 powers down the Bluetooth 42 and processor 44 circuitry (illustrated in FIG. 3 by a cross drawn through those features). The switch then provides power from the battery 46 in the dock to the prosthetic hand 10 (as the prosthetic hand may not have its own power supply). Instead of, or in addition to, the battery 46, the dock 32 may have a power input so that its own power and the power for the prosthetic hand 10 may come from an external supply, such as a power adaptor (not shown). In dependence on its determination that the prosthetic hand 10 is operatively connected to the dock, the switch provides output control signals 59 arising from the input control signals to the prosthetic hand 10. The operative connection in this example is by physical connection, although it will be appreciated that in other embodiments, other forms of operative connection may be used, for example using wireless signals, for example using a connection established between Bluetooth module 42 and a Bluetooth module 22 in a prosthetic hand powered by other means.

In this way, the dock 32 controls the movement of the prosthetic hand 10 by providing control signals and (optionally) power 59 to the prosthetic hand 10.

In another embodiment, processor 44 may not be powered down and instead powered up so that it can process the input control signals to generate the output control signals.

In the same way as described with reference to FIG. 1 the computer 24 can be used with software 30 and user interface 32 to transfer the same profile 33 (that has been used by the patient in developing their skills and muscle tone using the virtual prosthetic device) from the computer via the Bluetooth dongle 28 to the Bluetooth module 22 in the prosthetic hand 10. After the processor 20 updates the firmware in the prosthetic hand 10, the user can control the prosthetic hand 10 in the same way (using the same control signals) that they have been training using the virtual prosthetic hand. Alternatively, the transfer of the profile could be performed without using the dock 32. For example the prosthetic hand 10 could be connected to and powered by a socket (as shown in FIG. 1) when the profile transfer takes place.

Figure 4:
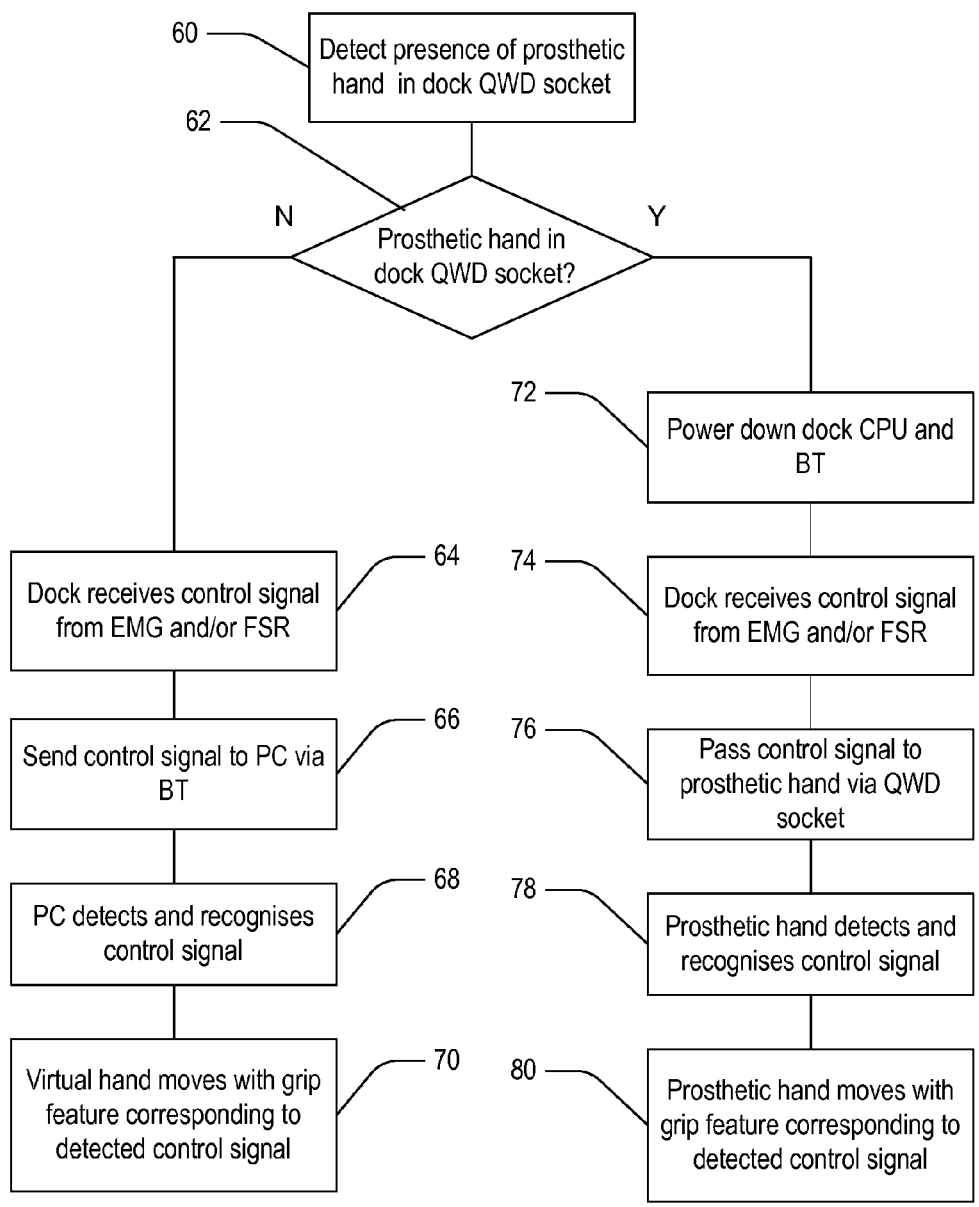
FIG. 4 illustrates a method of controlling a prosthetic device in accordance with an embodiment of the present invention.

FIG. 4 is a flow chart illustrating the operation of the prosthetic device control system, apparatus and method according to embodiments of the present invention.

60: the presence of a prosthetic hand in the dock's QWD socket is detected.

62: depending on whether or not it is determined if the prosthetic device is operatively connected to the dock, the input control signals are used to control either the computer model (steps 64-70) or to control movement of the prosthetic hand (steps 72-80).

When it is determined that the prosthetic hand is not in the dock, the following steps, corresponding to FIG. 2, are performed:

64: the dock 32 receives input control signals from electrodes 16 and/or force sensitive resistors 36.

66: the dock 32 sends output control signals to the computer 24 via the Bluetooth circuitry 42.

68: the computer 24 detects and recognises the control signal that it receives with its Bluetooth dongle 28. The computer program 58 comprises instructions which when executed by the processor 26 in the computer 24 cause the processor to control the computer model 52 using the received controlled signals 50.

70: the virtual hand 54 moves in accordance with the grip feature corresponding to the received control signal (in accordance with the profile currently in use in the computer).

If it is determined that the prosthetic hand is operably connected in the dock QWD socket, the following steps are (72-80) performed. These steps correspond to FIG. 3:

72: the switch 40 powers down the dock's Bluetooth 42 and processor 44 circuitry.

74: the dock receives input control signals from the electrodes 16 and/or the force sensitive resistors 36.

76: the switch 40 passes the input control signals to the prosthetic hand 10 (and provides power if required) via the quick wrist disconnect (QWD) socket 48.

78: the processor 20 in the prosthetic hand 10 detects and recognises the control signals.

80: the prosthetic hand 10 then moves with a grip feature corresponding to the detected control signal, in accordance with the profile stored in the firmware of the prosthetic hand 10.

Figure 5:
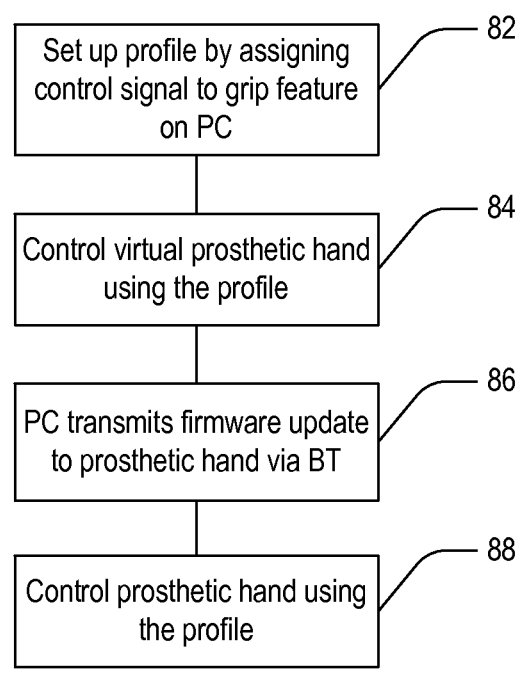
FIG. 5 illustrates using the same profile (of control signal assignments to grip features) to control both a computer model and a prosthetic device.

With reference to FIG. 5, the use of the same profile both to control the computer model and to be sent to the prosthetic device (for control of the prosthetic device) is shown:

82: the profile is set up by assigning control signals to grip features on the computer 24.

84: the virtual prosthetic hand is controlled using the profile (as shown in FIG. 2).

86: the computer transmits the profile, for example as a firmware update, to the prosthetic hand via Bluetooth (as shown in FIG. 3).

88: with the prosthetic hand's firmware updated, the patient controls the prosthetic hand using the same profile that they have been using to control the virtual prosthetic hand (as shown in FIG. 3).

Figures 6A, 6B:
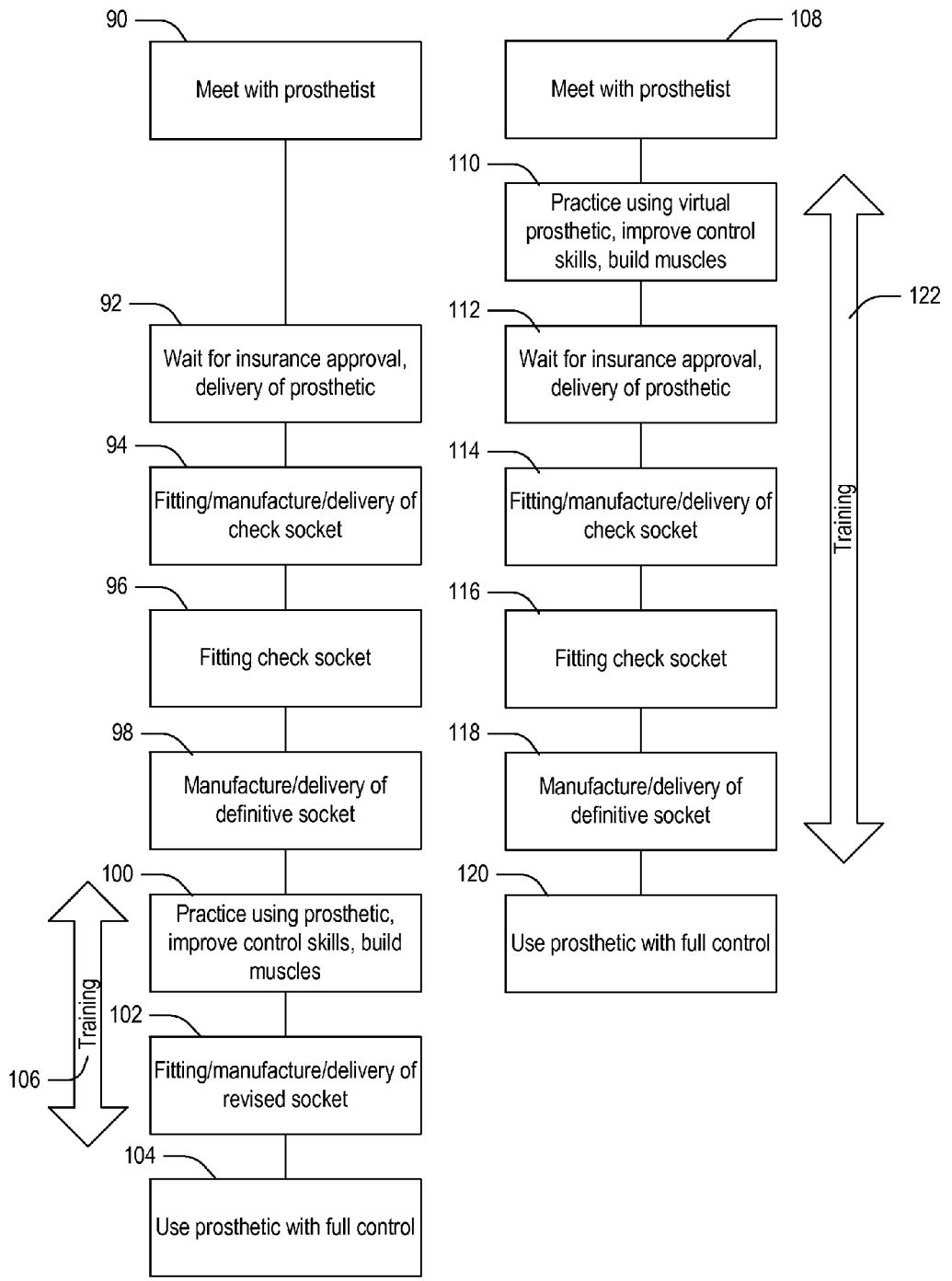
FIG. 6a illustrates the stages a patient goes through from a meeting prosthetist to using a prosthesis with full control, in accordance with the prior art.
FIG. 6b illustrates the stages that a patient goes through from meeting with a prosthetist to use of a prosthetic with full control, with the benefit of embodiments of the present invention.

With reference to FIG. 6a, the stages that a patient goes through without the benefit of embodiments of the present invention is shown:

90: the patient meets with the prosthetist.

92: the patient waits for insurance approval and (optionally at this stage) delivery of the prosthetic device.

94: the patient undergoes a fitting (this may be performed earlier, for example in step 90) and the patient waits for manufacture and delivery of a check socket. A check socket is a first attempt at providing a socket that fits the residual limb of the patient comfortably.

96: the check socket is fitted by the prosthetist and measurements are taken to enable improvements to the fit to be made in the subsequent definitive socket.

98: the patient waits for the manufacture and delivery and final fitting of the definitive socket.

100: on delivery and final fitting, the patient is at last able to start training 106 and practice using the prosthetic device to improve their control skills and to build muscles.

102: some patients will, after practice, build their muscle tone to such an extent that their socket becomes uncomfortable. Therefore a further round of fitting, manufacturing and delivery of a revised socket is necessary in some cases. This is very inconvenient for the patient and is costly because it involves new work, materials and further involvement of occupational therapists and prosthetists.

104: finally, the patient can use their prosthetic with full control.

With reference to FIG. 6b, an improved, shorter, patient experience is illustrated, which demonstrates the benefits provided by embodiments of the present invention:

108: the patient meets with the prosthetist.

110: the patient is provided with a prosthetic device control apparatus (in this example a dock) in accordance with an embodiment of the present invention. The prosthetist can use the dock to demonstrate a working prosthetic device, for example a demonstration prosthetic hand. The prosthetist can leave the dock with the patient and take the expensive hand, which is used exclusively for demonstrations, away. In accordance with embodiments of the present invention, the patient can begin to practice using the virtual prosthetic device (i.e. the computer model) and can start to improve their control skills and build their muscle tone.

112: while the patient is waiting for insurance approval, a process that can take several months, and delivery of the prosthetic the patient benefits from continuing to practice using the virtual prosthetic and continues to improve control skills and build muscles. This benefit for the patient is provided by embodiments of the present invention throughout not only this step but also the subsequent steps 114, 116 and 118 described below.

114: the fitting, manufacture and delivery of the check socket is performed in the same way as described with reference to FIG. 6a.

116: the fitting of the check socket is performed in the same way as described with reference to FIG. 6a.

118: the manufacture, delivery and fitting of a definitive socket is performed as described with reference to FIG. 6a.

120: the patient is now able to use their definitive socket as soon as it arrives with full control, having already built up their muscle tone and control skills. In contrast to the stages described in FIG. 6a, the problem of building muscle tone, developing an uncomfortable socket fit and requiring a revised socket is avoided.

Furthermore, the quality of life of the patient is improved because they can start to use their prosthetic with full control straight away, having performed their training 122 for delivery of the definitive socket.

Figure 7:
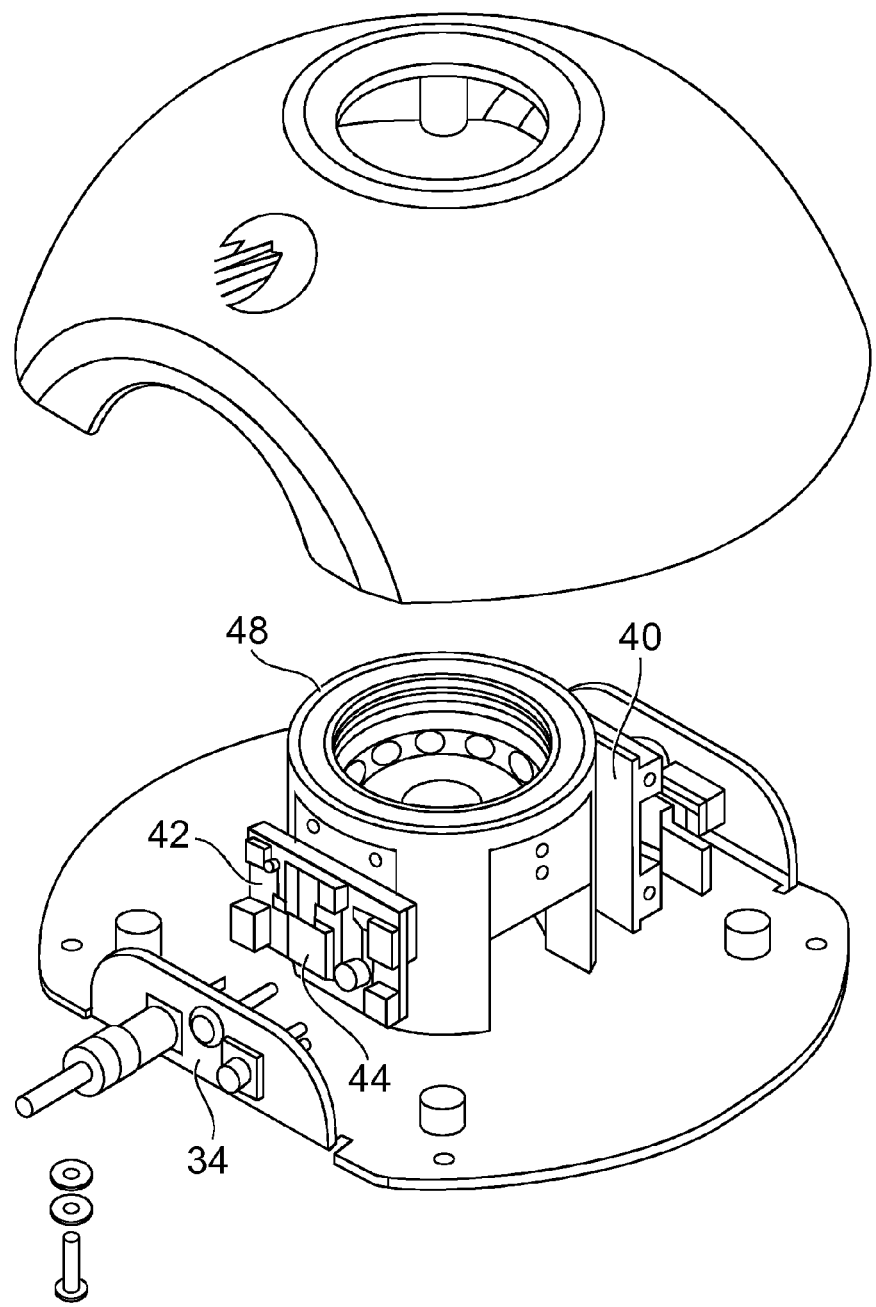
FIG. 7 illustrates a prosthetic device control apparatus in accordance with an embodiment of the present invention.

FIG. 7 illustrates a dock in accordance with an embodiment of the present invention. The numbering corresponds to features identified in FIGS. 2 and 3.

Further modifications and improvements may be added without departing from the scope of the invention herein described.

The invention claimed is:

1. A method of controlling a prosthetic device, the method including:
   providing the prosthetic device operable to move responsive to control signals;
   providing a processor executing a program comprising a computer model of the prosthetic device, the computer model operable to simulate movement of the prosthetic device responsive to the control signals;
   providing a prosthetic device control dock comprising;
      an input terminal for connection to a user input device, the input terminal receiving control signals from the user input device;
      a mechanical prosthetic quick disconnect socket having input and output connectors and configured to transmit control signals from the prosthetic device control dock input terminal to one of the prosthetic device and the processor executing the computer model;
   receiving, by the prosthetic device control dock, control signals from the user input device;
   determining, by the prosthetic device control dock, if the prosthetic device is operatively connected to the prosthetic device control dock; and
   depending on the determination, transmitting the control signals received by the prosthetic device control dock to either the processor executing the computer model or to the prosthetic device.

2. The method of claim 1, wherein if the prosthetic device is not operatively connected, transmitting the control signals received by the prosthetic control dock to the processor executing the computer model to simulate the movement of the prosthesis.

3. The method of claim 1 further including, if the prosthetic device is operatively connected, controlling the movement of the prosthetic device by the prosthetic device control dock providing power to the prosthetic device and providing output control signals arising from the control signals received by the prosthetic device control dock to the prosthetic device.

4. The method of claim 3 wherein if the prosthetic device is operatively connected, powering down, by the prosthetic device control dock, circuitry operable to provide control signals to the processor operable to control the computer model.

5. The method of claim 1 wherein the prosthetic control dock generates a profile of control signal assignments to grip features to control the computer model and using the same profile to control the movement of the prosthetic device.

6. The method of claim 1 wherein the input control signals comprise myoelectric signals.

7. The method of claim 1 wherein the user input device is a set of myoelectrodes for location on the limb of the patient.

8. The method of claim 1 wherein the user input device is a force sensitive key pad.

* * * * *